(12) United States Patent
Lamers et al.

(10) Patent No.: US 8,020,573 B2
(45) Date of Patent: Sep. 20, 2011

(54) MICROFLUIDIC CHANNELS AND RESERVOIRS IN PORTABLE ELECTRONIC DEVICES

(75) Inventors: Kristina L. Lamers, Fort Collins, CO (US); R. Shane Fazzio, Loveland, CO (US)

(73) Assignee: Avago Technologies Wireless IP (Singapore) Pte. Ltd., Singapore (SG)

( * ) Notice: Subject to any disclaimer, the term of this patent is extended or adjusted under 35 U.S.C. 154(b) by 1070 days.

(21) Appl. No.: 11/502,275

(22) Filed: Aug. 10, 2006

(65) Prior Publication Data

US 2008/0035207 A1    Feb. 14, 2008

(51) Int. Cl.
*E03B 1/00* (2006.01)

(52) U.S. Cl. ............ 137/7; 137/12; 137/87.01; 137/88; 455/66.1

(58) Field of Classification Search .......... 455/66.1; 435/40.5, 287.2; 422/58; 506/39; 361/690; 222/154.1; 137/7, 12, 87.1, 88
See application file for complete search history.

(56) References Cited

U.S. PATENT DOCUMENTS

| | | | |
|---|---|---|---|
| 4,882,245 A | 11/1989 | Gelorme et al. | |
| 5,644,342 A | 7/1997 | Argyres | |
| 6,390,453 B1 | 5/2002 | Frederickson et al. | |
| 6,712,287 B1 | 3/2004 | Le Pesant et al. | |
| 6,932,502 B2 | 8/2005 | Childers et al. | |
| 7,310,539 B2 | 12/2007 | Chiang et al. | |
| 7,402,279 B2* | 7/2008 | Schembri | 422/58 |
| 2002/0022261 A1 | 2/2002 | Anderson et al. | |
| 2002/0039280 A1* | 4/2002 | O'Connor et al. | 361/690 |
| 2002/0176802 A1 | 11/2002 | Chung et al. | |
| 2002/0177238 A1* | 11/2002 | Karp et al. | 436/180 |
| 2004/0022677 A1 | 2/2004 | Wohlstadter et al. | |
| 2004/0087008 A1* | 5/2004 | Schembri | 435/287.2 |
| 2004/0087033 A1* | 5/2004 | Schembri | 436/180 |
| 2004/0204043 A1 | 10/2004 | Wang | |
| 2004/0214056 A1 | 10/2004 | Gore | |
| 2004/0235430 A1 | 11/2004 | Ma et al. | |
| 2005/0258133 A9 | 11/2005 | Maynard | |
| 2006/0037970 A1* | 2/2006 | Fazzio et al. | 222/145.1 |
| 2006/0062408 A1 | 3/2006 | Cho et al. | |
| 2006/0148407 A1 | 7/2006 | Lin | |
| 2007/0154980 A1* | 7/2007 | Gasper et al. | 435/40.5 |
| 2007/0245559 A1 | 10/2007 | Feinn et al. | |
| 2008/0020794 A1* | 1/2008 | Garon et al. | 455/556.1 |
| 2008/0035207 A1 | 2/2008 | Lamers et al. | |

FOREIGN PATENT DOCUMENTS

| | | |
|---|---|---|
| DE | 20115776 | 3/2002 |
| DE | 202005012181 | 2/2006 |
| JP | 2000/189243 | 7/2000 |
| JP | 2002/252686 | 9/2002 |
| JP | 2003/310740 | 11/2003 |
| JP | 2005/295206 | 10/2005 |
| JP | 2006/19794 | 1/2006 |
| KR | 100614967 | 8/2006 |
| WO | WO-02/15541 | 2/2002 |
| WO | WO-2006/042419 | 4/2006 |
| WO | WO 2006042419 A1 * | 4/2006 |

* cited by examiner

*Primary Examiner* — Edward Urban
*Assistant Examiner* — Golam Sorowar

(57) ABSTRACT

A microfluidic case and an electronic device including a microfluidic case are described.

13 Claims, 5 Drawing Sheets

MICROFLUIDIC CHANNELS AND RESERVOIRS IN PORTABLE ELECTRONIC DEVICES

CROSS-REFERENCE TO RELATED APPLICATIONS

The present application is related to: U.S. patent application Ser. No. 10/919,669 (U.S. Patent Publication 20060037970) to Fazzio, et al., filed Aug. 17, 2004 and entitled "Scented Material Dispense System for a Hand-Held Device" to Fazzio, et al; U.S. patent application Ser. No. 11/502,276 filed concurrently herewith and entitled "Electrically Addressable Liquid Dispenser" to Lamers, et al; and U.S. patent application Ser. No. 11/502,277 filed concurrently herewith and entitled "Etch-Stop Layer and Method of Use" to Lamers, et al. The disclosures of these applications are specifically incorporated herein by reference.

BACKGROUND

Portable electronic devices continue to increase and improve in both form and function. For example, mobile phones often include a video function in addition to their audio function. This video function ranges from a basic display to a video recorder. As such, the human senses of hearing and seeing are engaged by many portable electronic devices. However, the olfactory sense is normally not engaged through the use of many known electronic devices.

While the use of scents may be beneficial to the user's experience, there remains the ever-increasing desire for reductions in size and cost of many portable electronic devices. As such, the addition of many known scent dispensing devices is not feasible.

What is needed, therefore, is an apparatus that overcomes at least the shortcomings described above.

SUMMARY

In accordance with an illustrative embodiment, an electronic device includes a microfluidic case having at least one reservoir adapted to hold a fluid material. The case includes at least one channel coupled to each of the reservoirs at a first end of the channel and adapted to receive the fluid material; an opening at a second end of the channel adapted to eject the fluid material; and a mechanical actuator adapted to force the fluid through the opening.

In accordance with another illustrative embodiment, a microfluidic case adapted for use with an electronic device includes at least one reservoir adapted to hold a fluid material. The case also includes at least one channel coupled to each reservoir at a first end of the channel and adapted to receive the fluid material; an opening at a second end of the channel adapted to eject the fluid material; and a mechanical actuator adapted to force the fluid through the opening.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DEFINED TERMINOLOGY

The terms 'a' or 'an', as used herein are defined as one or more than one.

The term 'plurality' as used herein is defined as two or more than two.

DETAILED DESCRIPTION

In the following detailed description, for purposes of explanation and not limitation, specific details are set forth in order to provide a thorough understanding of example embodiments according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of apparati, materials and methods known to one of ordinary skill in the art may be omitted so as to not obscure the description of the example embodiments. Such methods, materials and apparati are clearly within the scope of the present teachings.

Figure 1A:
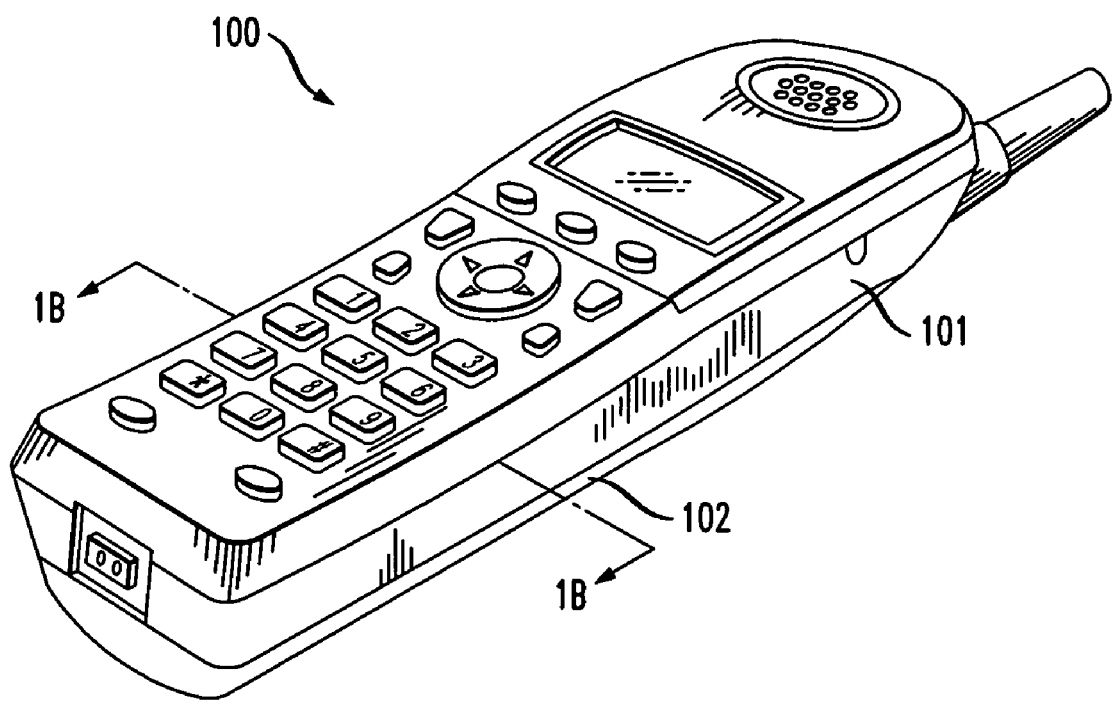
FIG. 1A is a perspective view of a portable electronic device in accordance with an illustrative embodiment.

FIG. 1A depicts an electronic device 100 in accordance with an illustrative embodiment. The device 100 shown is a mobile (cellular) telephone. However, the device 100 may be a personal digital assistant, a portable computer, a portable video player, a portable music player or a portable gaming device or a combination of one or more of these devices. It is emphasized that the noted devices are merely representative and that other devices within the purview of one of ordinary skill in the art are contemplated. Moreover, while the present description concentrates mainly on portable devices, the present teachings contemplate applications in traditionally non-portable devices such as home theatre; and traditionally non-electronic devices, such as the passenger compartment of an automobile. Again, the noted alternative applications are merely illustrative and in no way limiting of the applications of the present teachings.

The device 100 includes a body 101 that includes many of the components required for its function. The components alluded to include the various and sundry electronic and mechanical components found in known devices such as of the illustrative list noted above. The details of these devices are generally omitted in order to avoid obscuring the details of the present embodiments.

Attached to the body 101 is a microfluidic cover 102. In the present embodiment, the microfluidic cover 102 is friction-fit to the body using retention members such as clips (not shown). The retention members may be included on the body 101, or on the cover 102, or both. These retention members allow the affixing of the cover 102 to the body of the phone.

As will be described in greater detail herein, the microfluidic case 102 includes, inter alia, one or more reservoirs and one or more channels coupled to each reservoir. The reservoirs are adapted to hold fluid (e.g., liquid) material and the channels are adapted to deliver the fluid to openings or nozzles on the device 100 for the ejection of the fluid. In certain embodiments, the fluid material is a scented material such as perfume, or air freshener.

Figure 1B:
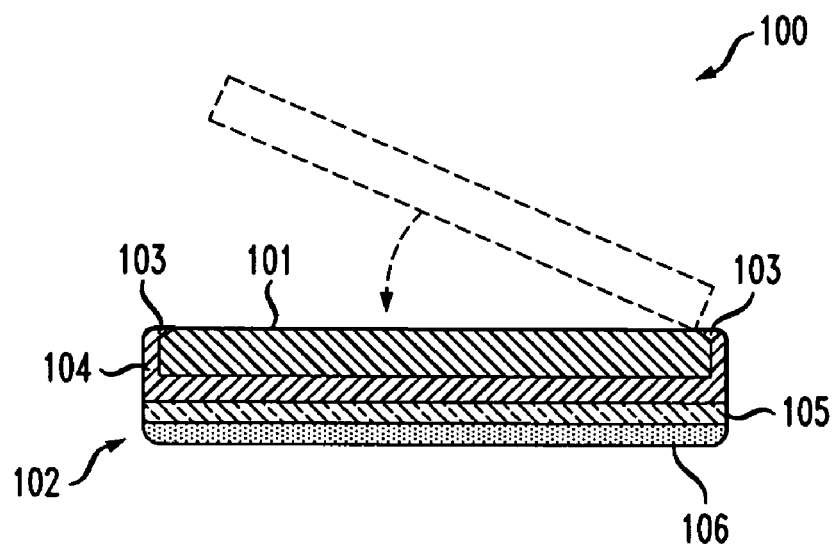
FIG. 1B is a cross-sectional view of a portable electronic device in accordance with an illustrative embodiment.

FIG. 1B is a cross-sectional view of the device 100 taken along the line 1B-1B shown in FIG. 1A. The body 101 is attached to the case 102 by retention members 103 that overlay the body 101 at least partially to ensure secure attachment of the body 101 to the case.

As shown by the arrow, the body 101 is rotated into engagement with the case 102 to complete the structure. The attachment of the case 102 to the body 101 is not necessarily permanent. As such, the case 102 may be disposable after use and replaced by another case. Moreover, the device 100 may be a 'clamshell' or 'flip-style' device. Thus, the body 101 may have the case 102 connected thereto, and a mating half (not shown) of the body 101 may hingeably engage the body 101 to complete the flip-style device.

In the present embodiment, the retention members 103 are part of a structural layer 104 of the case 102, and may be integral components thereof. The case 102 also includes a channel layer 105, which is disposed over the structural layer 104, and a sealing layer 106 disposed over the channel layer 105.

As described in greater detail herein, the channel layer 105 includes reservoirs adapted to receive fluid material, and channels adapted to transport the fluid from the reservoir to the ambient environment as determined by the user. Moreover, the channel layer 105 may include or be connected to valves, pumps and other mechanical devices (not shown) used to effect the ejection of fluid materials. Finally, the channel layer 105 may include or be connected to electronic components adapted to effect the ejection of the fluid materials. Details of these electronic components may be found in the cross-referenced patent application and publication noted previously.

The sealing layer 106 is provided over the channel layer 105 to maintain the fluid (e.g., liquid) in the reservoirs and channels, thereby substantially preventing leakage of the liquid and the loss thereof.

In an representative embodiment, the structural layer 104 is a polymer material and may be formed by injection molding, embossing or other suitable polymer forming process.

In a representative embodiment, the channel layer 105 is formed by a known dry film or spray application of a photoimageable polymer material. An optically opaque patterned layer is provided over the photoimageable layer and exposed (e.g., to UV radiation). The opaque layer is then removed and developer chemicals are applied to create channels and reservoirs in the desired number, location spacing and depth in the channel layer 105. As the details of the noted fabrication sequence are generally known to those skilled in the art, details are omitted in order to avoid obscuring the present disclosure.

In a representative embodiment, the sealing layer 106 is a polymer layer disposed over the channel layer 105 to seal the channels and reservoirs. The polymer may be dryfilm rolled or sprayed over the channel layer using materials and methods known to those of ordinary skill in the art.

Notably, the described materials and methods of fabricating the channel layer 105 are merely illustrative and it is emphasized that other methods are contemplated. For example, the channel layer 105 may be a semiconductor layer, or a glass layer, or other layer of material adapted to micromachining techniques such as deep reactive ion etching (DRIE) or other methods known to those skilled in the microelectromechanical systems (MEMS) fabrication arts, and the integrated circuit fabrication arts.

Figure 1C:
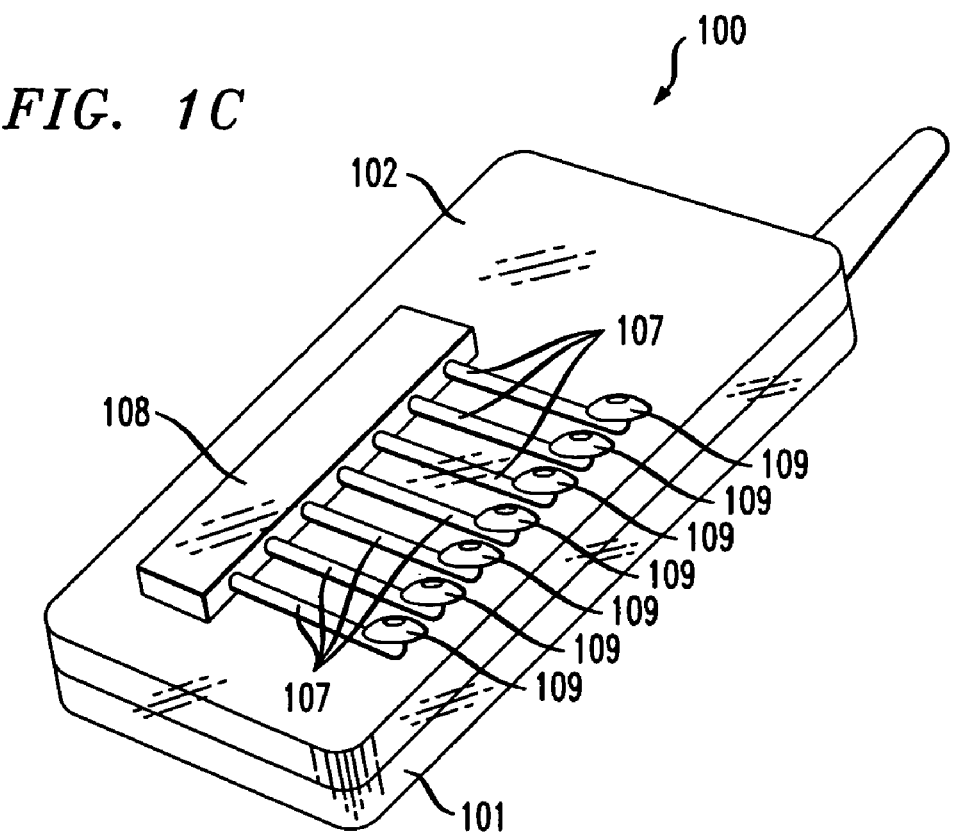
FIG. 1C is a perspective view a portable electronic device in accordance with an illustrative embodiment.

FIG. 1C is a perspective view of the portable electronic device 100. This view may be, for example a rear view showing the case 102 attached to the body. Alternatively, rather than a detachable case, the case 102 may be integral with the body 101 of the device 100. For example, the body 101 of the device 100 may include the microfluidic reservoirs, channels, electronic and mechanical components that are needed.

The case 102 includes a plurality of microfluidic channels 107 coupled to a reservoir 108. Each channel includes a nozzle 109 that allows fluid from the reservoir 108 to be emitted upon actuation. In the present embodiment, the case 102 is on the rear/back side of the device 100 and the nozzles 109 open to the back of the device 100. As will become clearer as the present description continues, the nozzles 109 may open to the opposite side of the case 102 than shown in FIG. 1C. Thereby, the nozzles 109 provide fluid from the reservoirs 108 via channels 107 to the front of the device 100. Moreover, nozzles 109 may be disposed on the sides of the device 100, or on a combination of the rear, front and sides of the device 100.

In accordance with illustrative embodiments, the reservoir 108 may include a single type of fluid or a mixture of different fluids. In certain embodiments, the fluid may be one or more scented fluids selected by the user. In another embodiment, the case 102 may include only one channel 107 and one nozzle 109.

It is noted that the sealing layer 106 disposed over microfluidic channels is not distinguished in FIG. 1C to aid in the description of the channels 107 and reservoir 108. This layer may be substantially transparent, opaque or only partially transparent.

Figure 2A:
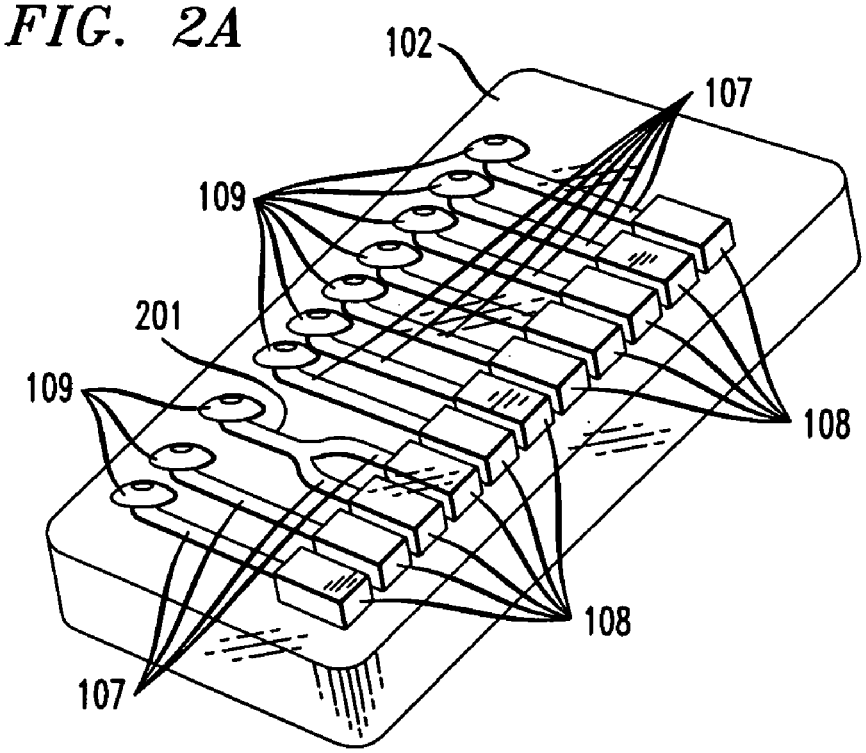
FIG. 2A is a perspective view of a microfluidic case in accordance with an illustrative embodiment.

FIG. 2A is a perspective view of a microfluidic case 102 in accordance with another illustrative embodiment. The case 102 shares many features described in connection with other illustrative embodiments, and such features are not repeated.

As in the embodiment of FIG. 1C, the case 102 includes a plurality of channels 107. However, in the present embodiment, there is also a plurality of reservoirs 108, with one channel 107 coupled to one reservoir 108. Moreover, some channels 107 may be adapted to combine into another channel 201, so that the fluid from two reservoirs 108 can be combined and emitted from a common nozzle 109 as shown. Thereby, a mixture of fluids or a greater volume of fluid, or both, may be provided. While only two channels are combined into one channel in the present embodiment, variations are contemplated. For example, multiple sets of channels may be combined into channels in the case 102. Also, more than two channels may be combined into one channel. The former adaptation allows for mixing of fluid from multiple channels and the ejection of fluid from multiple nozzles; and the latter allows for mixing of fluids from more than two reservoirs.

The selective mixing of fluids may be carried out using a mechanical actuator (e.g., a pump) or by electrically addressing the selected reservoirs. The latter method may be as described in the incorporated application to Lamers, et al.

Figure 2B:
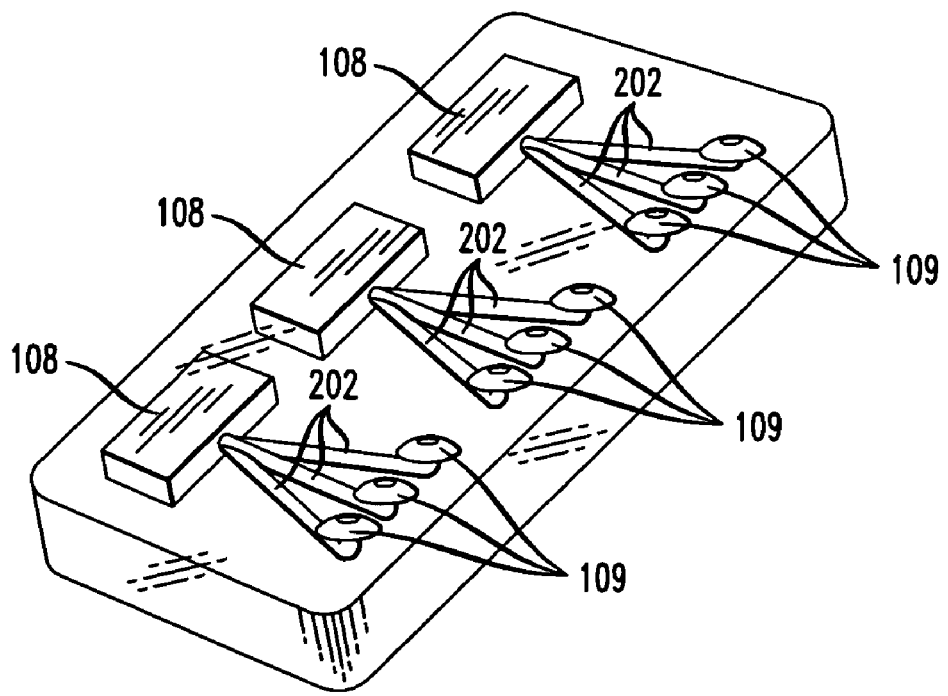
FIG. 2B is a perspective view of a microfluidic case in accordance with another illustrative embodiment.

FIG. 2B is a perspective view of a microfluidic case 102 in accordance with another illustrative embodiment. The case 102 shares many features described in connection with other illustrative embodiments, and such features are not repeated.

The case 102 of the presently described embodiment includes a plurality of reservoirs 108, with each having a plurality of channels 202 coupled thereto. The channels 202 are each coupled to nozzles 109 and are adapted to provide fluid from the reservoirs to selected nozzles 109, which are disposed to release the fluid from the rear of the device 100. Again, the ejection of fluid may be effected using mechanical or electrical actuation.

Mechanical actuation to release the fluid from selected reservoirs may be effected via micro-pumps provided in the channels and nozzles of the case. In an embodiment, a manually actuated elastic mechanism (e.g., a spring mechanism) provides the required pressure to overcome surface tension of the fluid in the reservoir/channel to eject the fluid through the selected nozzle(s) 109.

In another illustrative embodiment, the manually actuated elastic mechanism functions in concert with one or more ball valves in the channel. Using a ball (float) valve between the channel 107 and the reservoir 108 and another ball valve between the channel 107 and the nozzle, the application of a force to the elastic mechanism opens the ball valves and provides pressure to the fluid to release the fluid through the nozzle 109. Accordingly, elastic mechanisms (not shown) disposed on the case 102 are adapted to provide the liquid selectively from reservoirs 108 and respective nozzles 109.

The described mechanical actuation is intended to merely be illustrative and other mechanical and electrical actuators known by those skilled in the art are contemplated. Moreover, because the use of an elastic mechanism in concert with one or more valves is known to those skilled in the art, details are omitted in order to avoid obscuring the description of the embodiments.

Figure 3:
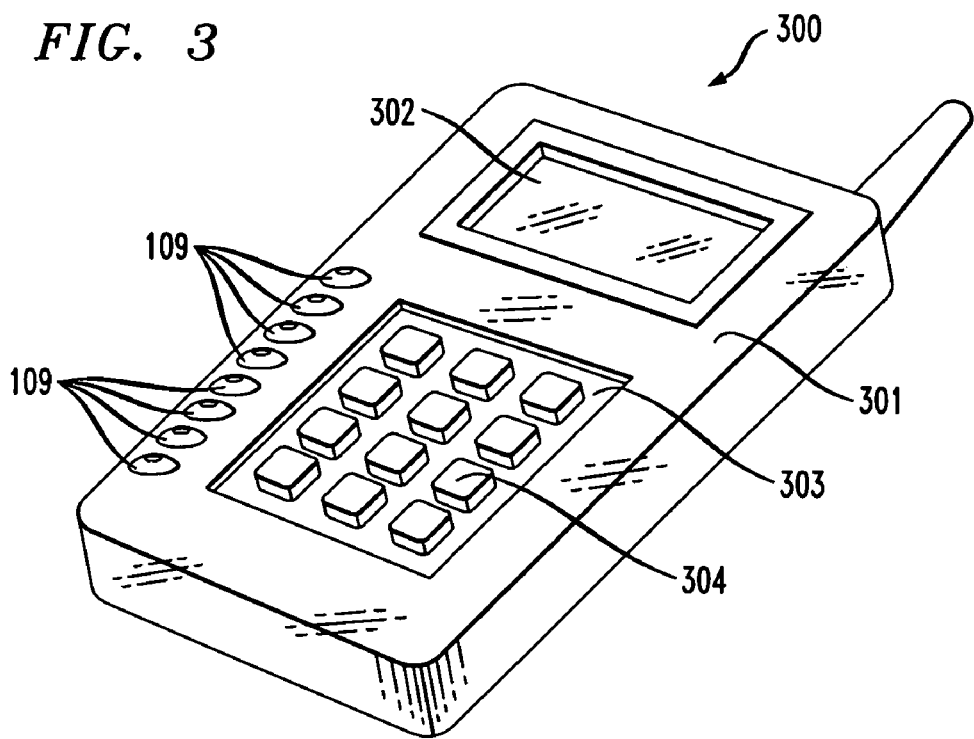
FIG. 3 is a perspective view of a portable electronic device in accordance with an illustrative embodiment.

FIG. 3 is a perspective view of an electronic device 300 in accordance with an illustrative embodiment. The device 300 has a microfluidic case 301 disposed thereover and substantially enveloping the body of the device 300.

The case 301 includes nozzles 109 adapted to release the fluid selectively from reservoirs and channels as described previously. The case also includes openings to allow viewing of a display 302 and an interface 303. The interface may include a plurality of buttons 304. These buttons 304 may be useful in interfacing with the electronics of the device and may be useful in effecting release of fluid(s) from the nozzles. For example, the buttons 304 may be used in concert with the display to engage selected fluids in selected reservoirs for release from the nozzles 109, or for the mixing of fluids prior to release, or both. Additional buttons may be provides for mechanical actuation to selectively release the fluid from reservoirs.

The cover 301 includes many of the features described previously in connection with embodiments of FIGS. 1A-2B. Most notably, the cover 301 may include the reservoir(s), channels and mechanical and electrical actuators described. In FIG. 3, a front side of the cover is shown. The rear side of the cover includes the channels, reservoirs described previously. Between the front and rear of the cover 301 is space for the body of the device 300, and conduits to the nozzles 109 if needed. Notably, the nozzles 109 may comprise an orifice (not shown) from the respective channels to the front side of the cover 301.

Figure 4A:
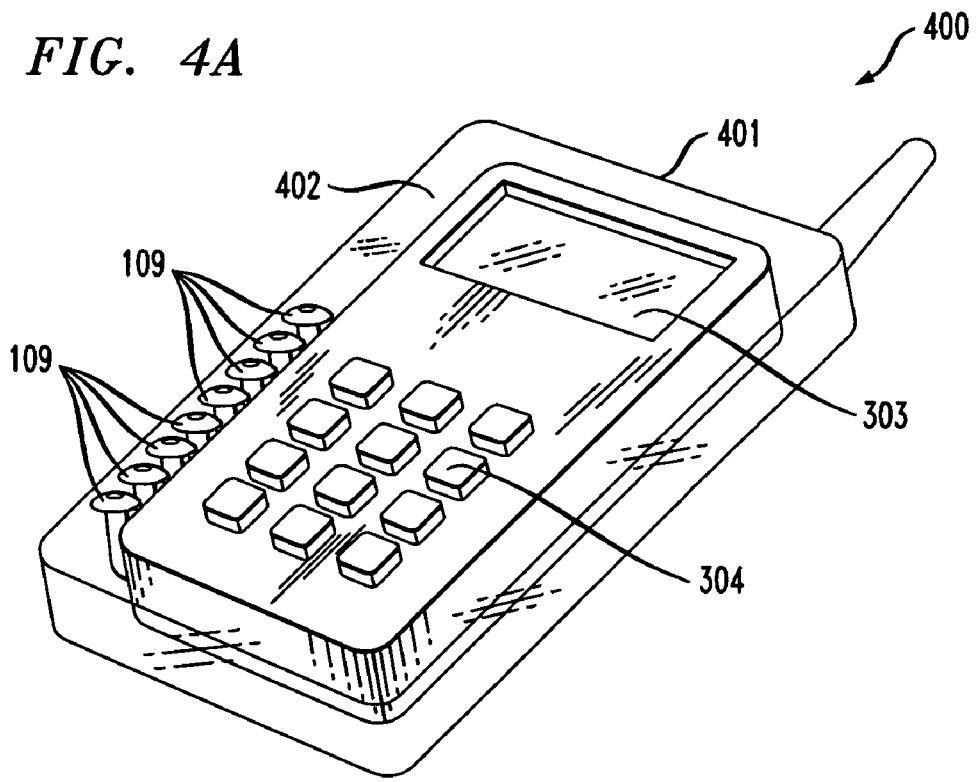
FIG. 4A is a perspective view of a portable electronic device in accordance with an illustrative embodiment.
Figure 4B:
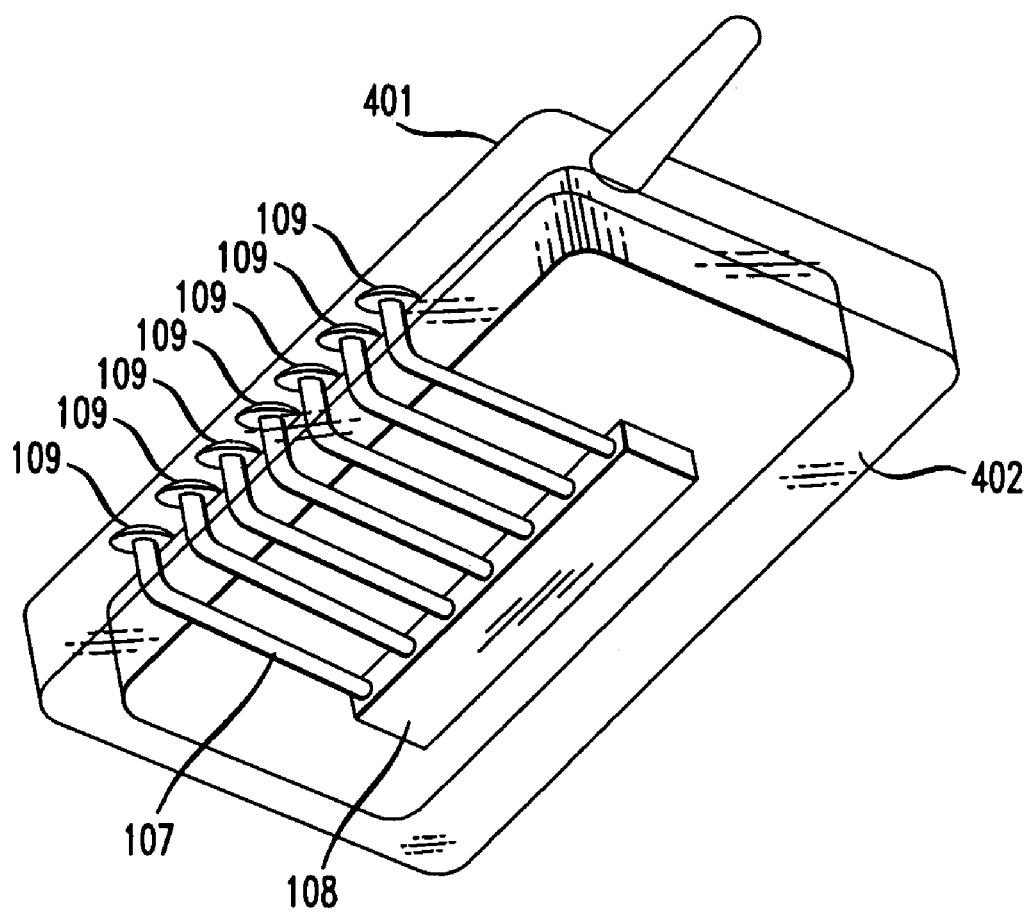
FIG. 4B is a perspective view of a portable electronic device in accordance with an illustrative embodiment.

FIGS. 4A and 4B are front and rear perspective views, respectively, of an electronic device 400 in accordance with an illustrative embodiment. The device 400 has a microfluidic case 401 disposed thereover and substantially enveloping the body of the device 400. In the present embodiment, the case 401 includes a portion 402 that is both substantially compliant and substantially transparent at least in the regions above the display 302 and the interface 303. The compliance of the material is useful in providing the elastic mechanism to force the fluid from the reservoirs and selected nozzles. The transparency of the material allows the functionality of the device 100 not to be compromised.

FIG. 4B shows the rear of the device 400 with the reservoir 108, channels 107 and nozzles 109 visible. As will be appreciated, the structure of the case 401 of FIG. 4B is substantially the same as that of the embodiments of FIGS. 1C-2B. Thus many of the features described in connection with these are found in the present embodiments. However, in addition to these features, the case 401 includes the portion 402 that is compliant. This material may be one of a variety of compliant polymer materials as well as other compliant materials known to one of ordinary skill in the art. As noted the portion 402 of the case 401 is also at least partially transparent. There are a variety of materials (e.g., polymers) that are both compliant and transparent.

In an illustrative embodiment, the cover 401 is fabricated as described above. The cover is then adhered to the portion 402 by known methods. Alternatively, the cover 401 may be integral comprised of a plurality of layers selectively bonded together using a process such as ultrasonic welding to form the reservoirs, channels and nozzles.

In connection with illustrative embodiments, an electronic device and a microfluidic case are described. One of ordinary skill in the art appreciates that many variations that are in accordance with the present teachings are possible and remain within the scope of the appended claims. These and other variations would become clear to one of ordinary skill in the art after inspection of the specification, drawings and claims herein. The invention therefore is not to be restricted except within the spirit and scope of the appended claims.

The invention claimed is:

1. An electronic device, comprising:
   a microfluidic case having at least one reservoir adapted to hold a fluid material, the case further comprising:
   at least one channel coupled to each reservoir at a first end of the channel and adapted to receive the fluid material;
   an opening at a second end of the channel adapted to eject the fluid material; and
   a mechanical actuator adapted to force the fluid through the second opening, wherein at least a portion of the microfluidic case is substantially compliant and is adapted to substantially envelope the electronic device.

2. An electronic device as claimed in claim 1, wherein the liquid material is a scented material.

3. An electronic device as claimed in claim 1, wherein the microfluidic case is adapted to be attached to and removed from the electronic device.

4. An electronic device as claimed in claim 1, wherein the microfluidic case is an integral component of a case of the electronic device.

5. An electronic device as claimed in claim 1, wherein the microfluidic case is at least partially substantially transparent.

6. An electronic device as claimed in claim 3, wherein the microfluidic case includes a structural layer, a channel layer and a sealing layer.

7. An electronic device as claimed in claim 1, wherein the at least one reservoir is single reservoir and the at least one channel comprises a plurality of channels coupled to the single reservoir.

8. A microfluidic case adapted for use with an electronic device, comprising:
   at least one reservoir adapted to hold a fluid material, comprising:
   at least one channel coupled to each of the reservoirs at a first end of the channel and adapted to receive the fluid material;

an opening at a second end of the channel adapted to eject the fluid material; and a mechanical actuator adapted to force the fluid through the second opening, wherein at least a portion of the microfluidic case is substantially compliant and is adapted to substantially envelope the electronic device.

9. A microfluidic cases claimed in claim 8, wherein the liquid material is a scented material.

10. A microfluidic case as claimed in claim 8, wherein the microfluidic case is adapted to be removed from and attached to the electronic device.

11. A microfluidic case as claimed in claim 8, wherein the microfluidic case is at least partially substantially transparent.

12. A microfluidic case as claimed in claim 10, wherein the microfluidic case includes a structural layer, a channel layer and a sealing layer.

13. A microfluidic case as claimed in claim 8, wherein the at least one reservoir is single reservoir and the at least one channel comprises a plurality of channels coupled to the single reservoir.

* * * * *